US00PP29325P2

(12) United States Plant Patent
Kardos

(10) Patent No.: US PP29,325 P2
(45) Date of Patent: May 29, 2018

(54) ***LAGERSTROEMIA* PLANT NAMED 'PIILAG-IX'**

(50) Latin Name: ***Lagerstroemia* hybrid**
Varietal Denomination: PIILAG-IX

(71) Applicant: Bailey Nurseries Inc., Newport, MN (US)

(72) Inventor: Joshua H. Kardos, Asheville, NC (US)

(73) Assignee: BAILEY NURSERIES INC., New Port, MN (US)

( * ) Notice: Subject to any disclaimer, the term of this patent is extended or adjusted under 35 U.S.C. 154(b) by 54 days.

(21) Appl. No.: 15/330,474

(22) Filed: Sep. 26, 2016

(51) Int. Cl.
*A01H 5/02* (2018.01)

(52) U.S. Cl.
USPC ..... Plt./252

(58) Field of Classification Search
USPC ..... Plt./252
See application file for complete search history.

*Primary Examiner* — Keith O Robinson
(74) *Attorney, Agent, or Firm* — Penny J. Aguirre

(57) ABSTRACT

A new cultivar of *Lagerstroemia* plant named 'PIILAG-IX' that is characterized by its compact and upright plant habit of intermediate stature, its freely branched growth habit without pruning resulting in a dense fine textured plant habit, its young stems that are grey-red in color, its foliage that is dark maroon-purple in color, and its flowers that are red in color.

2 Drawing Sheets

Botanical classification: *Lagerstroemia* hybrid.
Variety denomination: 'PIILAG-IX'.

BACKGROUND OF THE INVENTION

The present invention relates to a new and distinct cultivar of *Lagerstroemia* of hybrid origin. The new *Lagerstroemia* will hereafter be referred to by its cultivar name, 'PIILAG-IX'. 'PIILAG-IX' is a new cultivar of crape myrtle grown for use as an ornamental landscape plant.

The new cultivar was derived from a controlled breeding program conducted by the Inventors in Watkinsville, Ga. The objective of the breeding program is to develop a new cultivar of crape myrtle with an intermediate plant habit, dark foliage and red flowers.

'PIILAG-IX' arose from a cross made in 2012 between *Lagerstroemia* hybrid 'PIILAG-V' (U.S. Plant Pat. No. 25,925) as the female parent and *Lagerstroemia* hybrid 'PIILAG-VI' (U.S. Plant Pat. No. 26,183) as the male parent. 'PIILAG-IX' was selected as a single unique plant in 2014 from amongst the seedlings derived from the above cross.

Asexual propagation of the new cultivar was first accomplished by semi-hardwood stem cuttings by one of the Inventors in Watkinsville, Ga. in 2014. Asexual propagation by semi-hardwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PIILAG-IX' as a unique cultivar of *Lagerstroemia*.

1. 'PIILAG-IX' exhibits a compact and upright plant habit of intermediate stature.

2. 'PIILAG-IX' exhibits a freely branched growth habit without pruning resulting in a dense fine textured plant habit.
3. 'PIILAG-IX' exhibits foliage that is dark maroon-purple in color.
4. 'PIILAG-IX' exhibits young stems that are grey-red in color.
5. 'PIILAG-IX' exhibits flowers that are red in color.

'PIILAG-V', the female parent of 'PIILAG-IX', differs from 'PIILAG-IX' in having a more rounded plant habit and in having dark pink flowers. 'PIILAG-VI', the male parent of 'PIILAG-IX', differs from 'PIILAG-IX' in having orange-red new growth that matures to a dark-green and young stems that are orange-red in color, whereas 'PIILAG-IX' has grey purple leaves on both new and mature foliage and the young stems are grey-red. 'PIILAG-IX' can also be compared to the *Lagerstroemia* cultivar 'PIILAG-VII' (U.S. Plant Pat. No. 27,303). 'PIILAG-VII' differs from 'PIILAG-IX' in having a denser growth habit, new growth that is red in color, dark green leaves in the summer, and red flowers with petals that cover the stamens (stamens are visible for 'PIILAG-IX').

BRIEF DESCRIPTION OF THE DRAWINGS

The accompanying colored photographs illustrate the overall appearance and distinct characteristics of the new 'PIILAG-IX'. The photographs were taken of a 3 year-old plant of 'PIILAG-IX' as grown outdoors in a trial garden in Watkinsville, Ga.

The photograph in FIG. 1 provides a side view of 'PIILAG-IX' in bloom.

Figure 1:
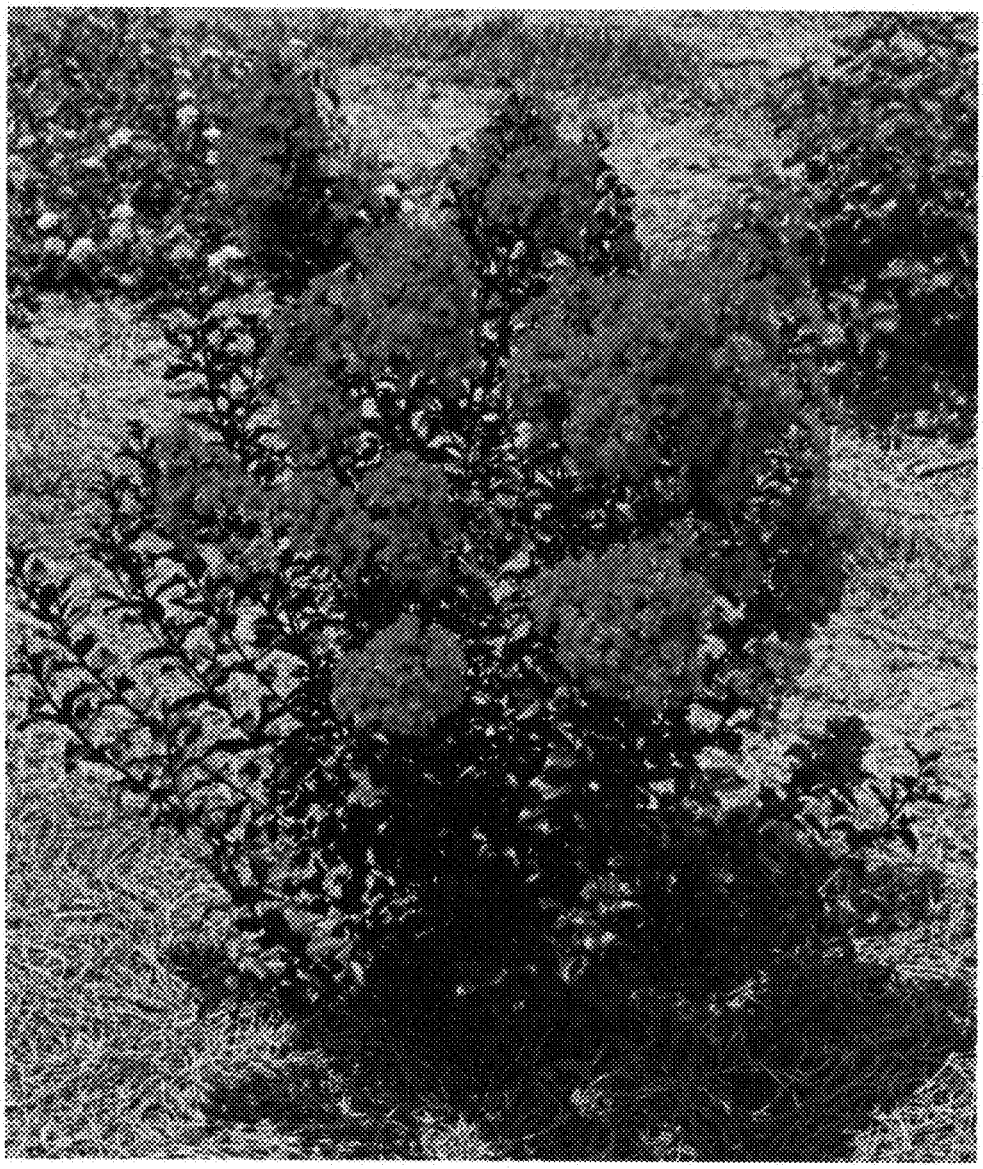
Figure 2:
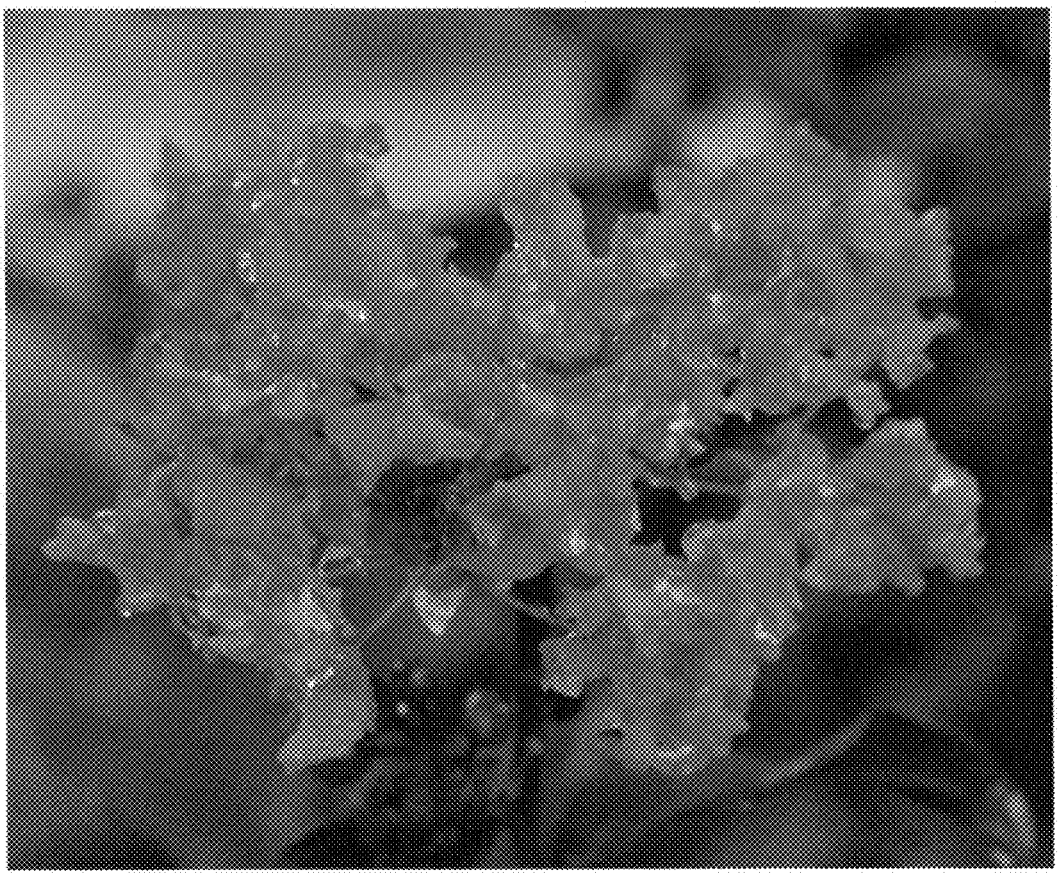

The photograph in FIG. 2 provides a close-up view of an inflorescence of 'PIILAG-IX'.

The colors in the photographs are as close as possible with the photographic and printing technology utilized and the color values cited in the Detailed Botanical Description accurately describe the colors of the new *Lagerstroemia*.

DETAILED BOTANICAL DESCRIPTION

The following is a detailed description of 3 year-old plants of the new cultivar as grown outdoors in a trial garden in Watkinsville, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—June to September in Watkinsville, Ga., deadheading will result in re-bloom 8 to 10 weeks later.

*Plant type.*—Deciduous, perennial shrub.

*Plant habit.*—Compact and upright plant habit of intermediate stature, fine textured and dense.

*Height and spread.*—An average of 91 cm in height and 74 cm in width as a 3 year-old plant in the landscape.

*Hardiness.*—At least in U.S.D.A. Zones 7 to 9.

*Diseases and pests.*—Resistance to powdery mildew (*Erysiphe lagerstoemia*) and leaf spot (*Cercospora lythracearum*) has been observed.

*Root description.*—158A in color, young roots are fibrous and fine, older roots become woody.

*Root development.*—An average of 6 weeks at 32° C. for root initiation and an average of 3 months at 32° C. to produce a young rooted plant.

*Propagation.*—Semi-hardwood vegetative stem cuttings.

*Growth rate.*—Vigorous.

Branch description:

*Branch shape.*—Tetragonal on first year growth and round on second year growth.

*Branch color.*—First year; 180A in color, second year; 164B, trunk; 164B.

*Branch size.*—Lateral branches; 48 to 91 cm in length and an average of 6 mm in diameter, trunk diameter; 1 cm measured 3 cm above soil level.

*Branch surface.*—Lateral branches moderately covered with coarse irregular lenticels 177C in color, trunk fine barked.

*Branch strength.*—Young; flexible and strong, mature; easily broken.

*Branching.*—Freely branching habit (without pruning) resulting in a fine textured appearance, an average of 7 lateral branches on a 3-year old plant.

*Branch aspect.*—Held at angles ranging between 45° to 75°.

*Internode size.*—An average of 1 cm.

*Stem fragrance.*—Fragrance typical for *Lagerstroemia* detected when touched (musty).

*Vegetative buds.*—Sub-opposite to alternate in arrangement, an average of 3 mm in length and 2 mm in width, imbricate, conical in shape, surface imbricate and lacks pubescence, color 185A.

Foliage description:

*Leaf shape.*—Elliptic.

*Leaf division.*—Single.

*Leaf base.*—Cuneate.

*Leaf apex.*—Acuminate.

*Leaf venation.*—Pinnate, upper and lower surfaces 185A in color.

*Leaf margins.*—Entire.

*Leaf arrangement.*—Sub-opposite to alternate.

*Leaf attachment.*—Petiolate.

*Leaf surface.*—Both surfaces glabrous and glossy.

*Leaf size.*—An average of 4 cm in length and 2 cm in width.

*Leaf quantity.*—An average of 84 per lateral branch.

*Leaf color.*—Young and mature leaves upper surface; N186A, young and mature leaves lower surface; N189A.

*Petiole.*—Average of 1.5 mm in length and 1 mm in diameter, surface texture glabrous, 184A in color.

Flower description:

*Inflorescence type.*—Terminal panicle.

*Lastingness of inflorescence.*—Inflorescence is showy for an average of 10 days, individual flowers last an average of 1 day, self cleaning.

*Inflorescence size.*—An average of 11 cm in height and 8 cm in width.

*Inflorescence number.*—One per lateral branch.

*Flower number.*—An average of 30 to 50 flowers and flower buds per inflorescence.

*Flower fragrance.*—Very faint sweet scent.

*Flower buds.*—Globose in shape, an average of 8 mm in length and depth, rounded apex, surface is glabrous with six distinct lines at petal margins, 146C in color with calyx portion 178A.

*Flower aspect.*—Upright to outward.

*Flower type.*—Rotate.

*Flower size.*—An average of 2.2 cm in diameter and 3.2 cm in depth.

*Petals.*—An average of 6, rotate in arrangement, reniform in shape, ruffled margins, sagittate base, ruffled and rounded apex, both surfaces glabrous, an average of 1.5 cm in length and 1.3 cm in width, color when opening and when fully open upper and lower surface; 45A.

*Calyx.*—Rotate in shape, an average of 9 mm in length and diameter, 178A in color.

*Sepals.*—An average of 6 petals, rotate arrangement, fused at base, rhomboidal in shape, entire margins, acuminate apex, both surfaces smooth and dull, an average of 9 mm in length and 4 mm in width, color of upper and lower surface when opening and when fully open 178A.

*Peduncles.*—Strong, an average of 9.3 cm in length and 2 mm in width, 181A in color, surface is satiny.

*Pedicels.*—Strong, an average of 8 mm in length and 2 mm in width, 183A in color, surface is satiny.

Reproductive organs:

*Stamens.*—25 to 30 short stamens surrounded by 6 longer stamens, anthers; an average of 1 mm in length, dorsifixed, narrow oblong in shape, 13A in color, filament; on short stamens an average of 7 mm in length and 37C in color, on long stamens an average of 1.3 cm in length and 44A in color, pollen is moderate in quantity and 7B in color.

*Pistils.*—1, an average of 1.9 cm in length, style; an average of 1.4 cm in length and 41C in color, stigma is club-shaped, 5 mm in length and 1 mm in diameter and 150C in color, ovary is superior, 10B in color and 2.5 mm in diameter.

*Fruit and seed.*—Capsule; 6-valved, dehiscent, capsules broad ellipsoidal in shape, 8 mm in length and diameter, immature 144A in color, mature 200C in color, each capsule contains numerous seeds an average of 5 mm in length and 3 mm in width and 200C in color.

It is claimed:

1. A new and distinct cultivar of *Lagerstroemia* plant named 'PIILAG-IX' as herein illustrated and described.

* * * * *